(12) United States Patent
Core

(10) Patent No.: US 7,766,820 B2
(45) Date of Patent: Aug. 3, 2010

(54) EXPANDABLE SHEATH TUBING

(75) Inventor: Lee A. Core, Cambridge, MA (US)

(73) Assignee: NMT Medical, Inc., Boston, MA (US)

( * ) Notice: Subject to any disclaimer, the term of this patent is extended or adjusted under 35 U.S.C. 154(b) by 989 days.

(21) Appl. No.: 10/693,398

(22) Filed: Oct. 24, 2003

(65) Prior Publication Data

US 2004/0087968 A1 May 6, 2004

Related U.S. Application Data

(60) Provisional application No. 60/421,436, filed on Oct. 25, 2002.

(51) Int. Cl.
*A61B 1/005* (2006.01)
(52) U.S. Cl. .................................................. 600/140
(58) Field of Classification Search ............... 623/1.11; 604/93.01, 262; 600/585
See application file for complete search history.

(56) References Cited

U.S. PATENT DOCUMENTS

| | | |
|---|---|---|
| 3,824,631 A | 7/1974 | Burstein et al. |
| 3,874,388 A | 4/1975 | King et al. |
| 3,875,648 A | 4/1975 | Bone |
| 3,924,631 A | 12/1975 | Mancusi, Jr. |
| 4,006,747 A | 2/1977 | Kronenthal et al. |
| 4,007,743 A | 2/1977 | Blake |
| 4,149,327 A | 4/1979 | Hammer et al. |
| 4,425,908 A | 1/1984 | Simon |
| 4,610,674 A | 9/1986 | Suzuki et al. |
| 4,626,245 A | 12/1986 | Weinstein |
| 4,693,249 A | 9/1987 | Schenck et al. ............. 128/334 |
| 4,696,300 A | 9/1987 | Anderson |
| 4,710,181 A | 12/1987 | Fuqua ........................ 604/280 |
| 4,710,192 A | 12/1987 | Liotta et al. |
| 4,738,666 A | 4/1988 | Fuqua ........................ 604/280 |
| 4,836,204 A | 6/1989 | Landymore et al. |
| 4,840,623 A | 6/1989 | Quackenbush |
| 4,902,508 A | 2/1990 | Badylak et al. |
| 4,915,107 A | 4/1990 | Rebuffat et al. |
| 4,917,089 A | 4/1990 | Sideris |
| 4,921,479 A | 5/1990 | Grayzel ........................ 604/53 |
| 4,956,178 A | 9/1990 | Badylak et al. |

(Continued)

FOREIGN PATENT DOCUMENTS

DE 9413645 U1 10/1994

(Continued)

OTHER PUBLICATIONS

International Search Report, International Application No. PCT/US03/17390 mailed Oct. 6, 2003 (4 pgs).

(Continued)

*Primary Examiner*—Kevin T Truong
(74) *Attorney, Agent, or Firm*—Helen S. Liu

(57) ABSTRACT

An introducer sheath or catheter can be formed in two or more layers with an inner layer made of a higher durometer material and an outer layer made of a lower durometer material. The inner layer can have one or a combination of the following: one or more longitudinal slits, overlapping portions, monolithic hinges, or other formations to allow for radial expansion.

43 Claims, 4 Drawing Sheets

U.S. PATENT DOCUMENTS

| | | | |
|---|---|---|---|
| 5,021,059 A | 6/1991 | Kensey et al. | |
| 5,037,433 A | 8/1991 | Wilk et al. | |
| 5,041,129 A | 8/1991 | Hayhurst et al. | |
| 5,049,131 A | 9/1991 | Deuss | 604/96 |
| 5,078,736 A | 1/1992 | Behl | |
| 5,106,913 A | 4/1992 | Yamaguchi et al. | |
| 5,108,420 A | 4/1992 | Marks | |
| 5,149,327 A | 9/1992 | Oshiyama et al. | |
| 5,152,144 A | 10/1992 | Andrie et al. | |
| 5,163,131 A | 11/1992 | Row et al. | |
| 5,167,363 A | 12/1992 | Adkinson et al. | |
| 5,167,637 A | 12/1992 | Okada et al. | |
| 5,171,259 A | 12/1992 | Inoue et al. | |
| 5,176,659 A * | 1/1993 | Mancini | 604/523 |
| 5,192,301 A | 3/1993 | Kamiya et al. | |
| 5,222,974 A | 6/1993 | Kensey et al. | |
| 5,226,879 A | 7/1993 | Ensminger et al. | |
| 5,236,440 A | 8/1993 | Hlavacek | |
| 5,245,023 A | 9/1993 | Peoples et al. | |
| 5,245,080 A | 9/1993 | Aubard et al. | |
| 5,250,430 A | 10/1993 | Peoples et al. | |
| 5,257,637 A | 11/1993 | El Gazayerli | |
| 5,275,826 A | 1/1994 | Badylak et al. | |
| 5,282,827 A | 2/1994 | Kensey et al. | |
| 5,284,488 A | 2/1994 | Sideris | |
| 5,304,184 A | 4/1994 | Hathaway et al. | |
| 5,312,341 A | 5/1994 | Turi | |
| 5,312,435 A | 5/1994 | Nash et al. | |
| 5,316,262 A | 5/1994 | Koebler | |
| 5,318,588 A * | 6/1994 | Horzewski et al. | 606/198 |
| 5,320,611 A | 6/1994 | Bonutti et al. | 604/264 |
| 5,334,217 A | 8/1994 | Das | |
| 5,350,363 A | 9/1994 | Goode et al. | |
| 5,354,308 A | 10/1994 | Simon et al. | |
| 5,364,356 A | 11/1994 | Höfling | 604/96 |
| 5,411,481 A | 5/1995 | Allen et al. | |
| 5,413,584 A | 5/1995 | Schulze et al. | |
| 5,417,699 A | 5/1995 | Klein et al. | |
| 5,425,744 A | 6/1995 | Fagan et al. | |
| 5,433,727 A | 7/1995 | Sideris | |
| 5,451,235 A | 9/1995 | Lock et al. | |
| 5,453,099 A | 9/1995 | Lee et al. | 604/282 |
| 5,478,353 A | 12/1995 | Yoon | |
| 5,480,353 A | 1/1996 | Garza, Jr. | |
| 5,480,424 A | 1/1996 | Cox | |
| 5,486,193 A | 1/1996 | Bourne et al. | |
| 5,507,811 A | 4/1996 | Koike et al. | |
| 5,534,432 A | 7/1996 | Peoples et al. | |
| 5,540,712 A | 7/1996 | Kleshinski et al. | |
| 5,562,632 A | 10/1996 | Davila et al. | |
| 5,577,299 A | 11/1996 | Thompson et al. | |
| 5,601,571 A | 2/1997 | Moss | |
| 5,603,703 A | 2/1997 | Elsberry et al. | 604/268 |
| 5,618,311 A | 4/1997 | Gryskiewicz | |
| 5,620,461 A | 4/1997 | Muijs Van De Moer et al. | |
| 5,626,599 A | 5/1997 | Bourne et al. | |
| 5,634,936 A | 6/1997 | Linden et al. | |
| 5,649,950 A | 7/1997 | Bourne et al. | |
| 5,649,959 A | 7/1997 | Hannam et al. | |
| 5,663,063 A | 9/1997 | Peoples et al. | |
| 5,683,411 A | 11/1997 | Kavteladze et al. | |
| 5,690,674 A | 11/1997 | Diaz | |
| 5,693,085 A | 12/1997 | Buirge et al. | |
| 5,702,421 A | 12/1997 | Schneidt et al. | |
| 5,709,707 A | 1/1998 | Lock et al. | |
| 5,713,864 A | 2/1998 | Verkaart | 604/113 |
| 5,717,259 A | 2/1998 | Schexnayder | |
| 5,720,754 A | 2/1998 | Middleman et al. | |
| 5,725,552 A | 3/1998 | Kotula et al. | |
| 5,733,294 A | 3/1998 | Forber et al. | |
| 5,733,337 A | 3/1998 | Carr, Jr. et al. | |
| 5,741,297 A | 4/1998 | Simon | |
| 5,746,696 A * | 5/1998 | Kondo | 600/139 |
| 5,772,641 A | 6/1998 | Wilson | 604/280 |
| 5,776,162 A | 7/1998 | Kleshinski | |
| 5,776,183 A | 7/1998 | Kanesaka et al. | |
| 5,797,960 A | 8/1998 | Stevens et al. | |
| 5,800,516 A | 9/1998 | Fine et al. | |
| 5,810,884 A | 9/1998 | Kim | |
| 5,820,594 A | 10/1998 | Fontirroche et al. | |
| 5,823,956 A | 10/1998 | Roth et al. | |
| 5,829,447 A | 11/1998 | Stevens et al. | |
| 5,853,422 A | 12/1998 | Huebsch et al. | |
| 5,855,614 A | 1/1999 | Stevens et al. | |
| 5,861,003 A | 1/1999 | Latson et al. | |
| 5,865,791 A | 2/1999 | Whayne et al. | |
| 5,879,366 A | 3/1999 | Shaw et al. | |
| 5,885,508 A * | 3/1999 | Ishida | 264/313 |
| 5,893,856 A | 4/1999 | Jacob et al. | |
| 5,902,287 A | 5/1999 | Martin | 604/280 |
| 5,902,319 A | 5/1999 | Daley | |
| 5,904,703 A | 5/1999 | Gilson | |
| 5,919,200 A | 7/1999 | Stambaugh et al. | |
| 5,924,424 A | 7/1999 | Stevens et al. | |
| 5,928,250 A | 7/1999 | Koike et al. | |
| 5,938,587 A * | 8/1999 | Taylor et al. | 600/139 |
| 5,944,691 A * | 8/1999 | Querns et al. | 604/104 |
| 5,944,738 A | 8/1999 | Amplatz et al. | |
| 5,955,110 A | 9/1999 | Patel et al. | |
| 5,976,174 A | 11/1999 | Ruiz | |
| 5,980,505 A | 11/1999 | Wilson | 604/525 |
| 5,989,268 A | 11/1999 | Pugsley, Jr. et al. | |
| 5,993,475 A | 11/1999 | Lin et al. | |
| 5,993,844 A | 11/1999 | Abraham et al. | |
| 5,997,575 A | 12/1999 | Whitson et al. | |
| 6,010,517 A | 1/2000 | Baccaro | |
| 6,019,753 A | 2/2000 | Pagan | 604/523 |
| 6,024,756 A | 2/2000 | Huebsch et al. | |
| 6,027,519 A | 2/2000 | Stanford | 606/198 |
| 6,030,007 A | 2/2000 | Bassily et al. | |
| 6,056,760 A | 5/2000 | Koike et al. | |
| 6,071,998 A | 6/2000 | Muller et al. | |
| 6,077,291 A | 6/2000 | Das | |
| 6,077,880 A | 6/2000 | Castillo et al. | |
| 6,079,414 A | 6/2000 | Roth | |
| 6,080,182 A | 6/2000 | Shaw et al. | |
| 6,096,347 A | 8/2000 | Geddes et al. | |
| 6,106,913 A | 8/2000 | Scardino et al. | |
| 6,113,609 A | 9/2000 | Adams | |
| 6,117,159 A | 9/2000 | Huebsch et al. | |
| 6,126,686 A | 10/2000 | Badylak et al. | |
| 6,132,438 A | 10/2000 | Fleischman et al. | |
| 6,143,037 A | 11/2000 | Goldstein et al. | |
| 6,152,144 A | 11/2000 | Lesh et al. | |
| 6,165,183 A | 12/2000 | Kuehn et al. | |
| 6,165,204 A | 12/2000 | Levinson et al. | |
| 6,168,588 B1 | 1/2001 | Wilson | 604/525 |
| 6,171,329 B1 | 1/2001 | Shaw et al. | |
| 6,174,322 B1 | 1/2001 | Schneidt et al. | |
| 6,174,330 B1 | 1/2001 | Stinson | |
| 6,183,443 B1 | 2/2001 | Kratoska et al. | 604/164.03 |
| 6,187,039 B1 | 2/2001 | Hiles et al. | |
| 6,190,353 B1 | 2/2001 | Makower et al. | |
| 6,190,357 B1 | 2/2001 | Ferrari et al. | 604/102.01 |
| 6,197,016 B1 | 3/2001 | Fourkas et al. | 604/537 |
| 6,199,262 B1 | 3/2001 | Martin | 29/525.15 |
| 6,206,895 B1 | 3/2001 | Levinson | |
| 6,206,907 B1 | 3/2001 | Marino et al. | |
| 6,214,029 B1 | 4/2001 | Thill et al. | |
| 6,217,590 B1 | 4/2001 | Levinson | |
| 6,221,092 B1 | 4/2001 | Koike et al. | |
| 6,227,139 B1 | 5/2001 | Nguyen et al. | |
| 6,228,097 B1 | 5/2001 | Levinson et al. | |
| 6,231,561 B1 | 5/2001 | Frazier et al. | |

| | | | | | | |
|---|---|---|---|---|---|---|
| 6,245,080 | B1 | 6/2001 | Levinson | 6,921,410 B2 | 7/2005 | Porter |
| 6,245,537 | B1 | 6/2001 | Williams et al. | 7,182,753 B2 * | 2/2007 | Matsumoto .................. 604/256 |
| 6,261,309 | B1 | 7/2001 | Urbanski | 2001/0010481 A1 | 8/2001 | Blanc et al. |
| 6,265,333 | B1 | 7/2001 | Dzenis et al. | 2001/0014800 A1 | 8/2001 | Frazier et al. |
| 6,270,515 | B1 | 8/2001 | Linden et al. | 2001/0034537 A1 | 10/2001 | Shaw et al. |
| 6,277,138 | B1 | 8/2001 | Levinson et al. | 2001/0034567 A1 | 10/2001 | Allen et al. |
| 6,277,139 | B1 | 8/2001 | Levinson et al. | 2001/0037129 A1 | 11/2001 | Thill |
| 6,287,317 | B1 | 9/2001 | Makower et al. | 2001/0039435 A1 | 11/2001 | Roue et al. |
| 6,290,674 | B1 | 9/2001 | Roue et al. | 2001/0041914 A1 | 11/2001 | Frazier et al. |
| 6,306,150 | B1 | 10/2001 | Levinson | 2001/0041915 A1 | 11/2001 | Roue et al. |
| 6,306,424 | B1 | 10/2001 | Vyakarnam et al. | 2001/0044639 A1 | 11/2001 | Levinson |
| 6,312,443 | B1 * | 11/2001 | Stone .......................... 606/198 | 2001/0049492 A1 | 12/2001 | Frazier et al. |
| 6,312,446 | B1 | 11/2001 | Huebsch et al. | 2002/0010481 A1 | 1/2002 | Jayaraman |
| 6,316,262 | B1 | 11/2001 | Huisman et al. | 2002/0019648 A1 | 2/2002 | Akerfeldt et al. |
| 6,319,263 | B1 | 11/2001 | Levinson | 2002/0022859 A1 | 2/2002 | Hogendijk .................. 606/200 |
| 6,322,548 | B1 | 11/2001 | Payne et al. | 2002/0026208 A1 | 2/2002 | Roe et al. |
| 6,328,727 | B1 | 12/2001 | Frazier et al. | 2002/0029048 A1 | 3/2002 | Miller |
| 6,334,872 | B1 | 1/2002 | Termin et al. | 2002/0032459 A1 | 3/2002 | Horzewski et al. |
| 6,342,064 | B1 | 1/2002 | Koike et al. | 2002/0032462 A1 | 3/2002 | Houser et al. |
| 6,344,048 | B1 | 2/2002 | Chin et al. | 2002/0034259 A1 | 3/2002 | Tada |
| 6,344,049 | B1 | 2/2002 | Levinson et al. | 2002/0035374 A1 | 3/2002 | Borillo et al. |
| 6,346,074 | B1 | 2/2002 | Roth | 2002/0043307 A1 | 4/2002 | Ishida et al. |
| 6,346,092 | B1 * | 2/2002 | Leschinsky .............. 604/96.01 | 2002/0052572 A1 | 5/2002 | Franco et al. |
| 6,348,041 | B1 | 2/2002 | Klint et al. | 2002/0058989 A1 | 5/2002 | Chen et al. |
| 6,352,552 | B1 | 3/2002 | Levinson et al. | 2002/0077555 A1 | 6/2002 | Schwartz |
| 6,355,052 | B1 | 3/2002 | Neuss et al. | 2002/0095174 A1 | 7/2002 | Tsugita et al. |
| 6,356,782 | B1 | 3/2002 | Sirimanne et al. | 2002/0096183 A1 | 7/2002 | Stevens et al. |
| 6,358,238 | B1 * | 3/2002 | Sherry .......................... 604/524 | 2002/0099389 A1 | 7/2002 | Michler et al. |
| 6,364,853 | B1 | 4/2002 | French et al. | 2002/0107531 A1 | 8/2002 | Schreck et al. |
| 6,371,904 | B1 | 4/2002 | Sirimanne et al. | 2002/0111537 A1 | 8/2002 | Taylor et al. |
| 6,375,625 | B1 | 4/2002 | French et al. | 2002/0111637 A1 | 8/2002 | Kaplan et al. |
| 6,375,671 | B1 | 4/2002 | Kobayashi et al. | 2002/0111647 A1 | 8/2002 | Khairkhahan et al. |
| 6,379,342 | B1 | 4/2002 | Levinson | 2002/0120323 A1 | 8/2002 | Thompson et al. |
| 6,379,368 | B1 | 4/2002 | Corcoran et al. | 2002/0128680 A1 | 9/2002 | Pavlovic |
| 6,387,104 | B1 | 5/2002 | Pugsley, Jr. et al. | 2002/0129819 A1 | 9/2002 | Feldman et al. |
| 6,398,796 | B2 | 6/2002 | Levinson | 2002/0164729 A1 | 11/2002 | Skraly et al. |
| 6,402,772 | B1 | 6/2002 | Amplatz et al. | 2002/0169377 A1 | 11/2002 | Khairkhahan et al. |
| 6,419,669 | B1 | 7/2002 | Frazier et al. | 2002/0183786 A1 | 12/2002 | Girton |
| 6,426,145 | B1 | 7/2002 | Moroni | 2002/0183787 A1 | 12/2002 | Wahr et al. |
| 6,436,088 | B2 | 8/2002 | Frazier et al. | 2002/0183823 A1 | 12/2002 | Pappu |
| 6,440,152 | B1 | 8/2002 | Gainor et al. | 2002/0198563 A1 | 12/2002 | Gainor et al. |
| 6,450,987 | B1 | 9/2002 | Kramer .......................... 604/43 | 2003/0004533 A1 | 1/2003 | Dieck et al. |
| 6,460,749 | B1 | 10/2002 | Levinson et al. | 2003/0023266 A1 | 1/2003 | Borillo et al. |
| 6,482,224 | B1 | 11/2002 | Michler et al. | 2003/0028213 A1 | 2/2003 | Thill et al. |
| 6,488,706 | B1 | 12/2002 | Solymar et al. | 2003/0045893 A1 | 3/2003 | Ginn |
| 6,494,846 | B1 | 12/2002 | Margolis .................... 600/585 | 2003/0050665 A1 | 3/2003 | Ginn |
| 6,494,888 | B1 | 12/2002 | Laufer et al. | 2003/0055455 A1 | 3/2003 | Yang et al. |
| 6,508,828 | B1 | 1/2003 | Akerfeldt et al. | 2003/0057156 A1 | 3/2003 | Peterson et al. |
| 6,514,515 | B1 | 2/2003 | Williams | 2003/0059640 A1 | 3/2003 | Marton et al. |
| 6,548,569 | B1 | 4/2003 | Williams et al. | 2003/0065379 A1 | 4/2003 | Babbs et al. |
| 6,551,303 | B1 | 4/2003 | Van Tassel et al. | 2003/0100920 A1 | 5/2003 | Akin et al. |
| 6,551,344 | B2 | 4/2003 | Thill | 2003/0120337 A1 | 6/2003 | Van Tassel et al. |
| 6,585,719 | B2 | 7/2003 | Wang .......................... 604/525 | 2003/0139819 A1 | 7/2003 | Beer et al. |
| 6,585,755 | B2 | 7/2003 | Jackson et al. | 2003/0171774 A1 | 9/2003 | Freudenthal et al. |
| 6,596,013 | B2 | 7/2003 | Yang et al. | 2003/0191495 A1 | 10/2003 | Ryan et al. |
| 6,599,448 | B1 | 7/2003 | Ehrhard, Jr. et al. | 2003/0195530 A1 | 10/2003 | Thill |
| 6,610,764 | B1 | 8/2003 | Martin et al. | 2003/0204203 A1 | 10/2003 | Khairkhahan et al. |
| 6,623,508 | B2 | 9/2003 | Shaw et al. | 2004/0044361 A1 | 3/2004 | Frazier et al. |
| 6,623,518 | B2 | 9/2003 | Thompson et al. | 2004/0073242 A1 | 4/2004 | Chanduszko |
| 6,626,936 | B2 | 9/2003 | Stinson | 2004/0176799 A1 | 9/2004 | Chanduszko et al. |
| 6,629,901 | B2 | 10/2003 | Huang | 2004/0210301 A1 | 10/2004 | Obermiller |
| 6,666,861 | B1 | 12/2003 | Grabek | 2004/0234567 A1 | 11/2004 | Dawson |
| 6,669,722 | B2 | 12/2003 | Chen et al. | 2005/0025809 A1 | 2/2005 | Hasirci et al. |
| 6,689,589 | B2 | 2/2004 | Huisman et al. | 2005/0043759 A1 | 2/2005 | Chanduszko |
| 6,712,804 | B2 | 3/2004 | Roue et al. | 2005/0113868 A1 | 5/2005 | Devellian et al. |
| 6,712,836 | B1 | 3/2004 | Berg et al. | 2005/0267523 A1 | 12/2005 | Devellian et al. |
| 6,726,696 | B1 | 4/2004 | Houser et al. | 2005/0273135 A1 | 12/2005 | Chanduszko et al. |
| 6,828,357 | B1 | 12/2004 | Martin et al. | 2005/0288786 A1 | 12/2005 | Chanduszko |
| 6,838,493 | B2 | 1/2005 | Williams et al. | 2006/0122647 A1 | 6/2006 | Callaghan et al. |
| 6,858,024 | B1 * | 2/2005 | Berg et al. .................. 604/525 | 2006/0265004 A1 | 11/2006 | Callaghan et al. |
| 6,867,247 | B2 | 3/2005 | Williams et al. | 2007/0010851 A1 | 1/2007 | Chanduszko et al. |
| 6,867,248 | B1 | 3/2005 | Martin et al. | | | |
| 6,867,249 | B2 | 3/2005 | Lee et al. | | | |

| | | |
|---|---|---|
| 2007/0167981 A1 | 7/2007 | Opolski |

FOREIGN PATENT DOCUMENTS

| | | |
|---|---|---|
| EP | 0362113 | 4/1990 |
| EP | 0474887 A1 | 3/1992 |
| EP | 0 839 549 | 5/1998 |
| EP | 1013227 A2 | 6/2000 |
| EP | 1046375 A2 | 10/2000 |
| EP | 1222897 A2 | 7/2002 |
| WO | WO-96/25179 A1 | 8/1996 |
| WO | WO-96/31157 A1 | 10/1996 |
| WO | WO-98/07375 A1 | 2/1998 |
| WO | WO-98/08462 | 3/1998 |
| WO | WO-98/16174 | 4/1998 |
| WO | WO-98/18864 | 5/1998 |
| WO | WO 98/29026 | 7/1998 |
| WO | WO-98/51812 | 11/1998 |
| WO | WO-99/05977 | 2/1999 |
| WO | WO-99/18862 | 4/1999 |
| WO | WO-99/18864 | 4/1999 |
| WO | WO-99/18870 | 4/1999 |
| WO | WO-99/18871 | 4/1999 |
| WO | WO-99/30640 | 6/1999 |
| WO | WO-00/27292 | 5/2000 |
| WO | WO-00/44428 A1 | 8/2000 |
| WO | WO-01/21247 | 3/2001 |
| WO | WO-01/30268 | 5/2001 |
| WO | WO-01/49185 | 7/2001 |
| WO | WO-01/78596 | 10/2001 |
| WO | WO-02/17809 | 3/2002 |
| WO | WO-02/24106 | 3/2002 |
| WO | WO-03/024337 | 3/2003 |
| WO | WO-03/053493 | 7/2003 |
| WO | WO-03/059152 | 7/2003 |
| WO | WO-03/063732 A | 8/2003 |
| WO | WO-03/077733 A2 | 9/2003 |
| WO | WO-03/082076 | 10/2003 |
| WO | WO-03/103476 | 12/2003 |
| WO | WO-2004/032993 | 4/2004 |
| WO | WO-2004/037333 | 5/2004 |
| WO | WO-2004/043266 | 5/2004 |
| WO | WO-2004/043508 | 5/2004 |
| WO | WO-2004/052213 | 6/2004 |
| WO | WO-2005/006990 | 1/2005 |
| WO | WO-2005/018728 | 3/2005 |
| WO | WO-2005/027752 | 3/2005 |
| WO | WO-2005/092203 | 10/2005 |
| WO | WO-2005/110240 | 11/2005 |
| WO | WO-2005/112779 | 12/2005 |
| WO | WO-2006/036837 | 4/2006 |
| WO | WO-2006/102213 | 9/2006 |

OTHER PUBLICATIONS

Kimura, A., et al., "Effects of Neutron Irradiation on the Transformation Behavior in Ti-Ni Alloys," Abstract, Proceedings of the Int'l Conf. on Marienstic Transformations, 1992, pp. 935-940.
Meier, MD, Bernhard, et al., "Contemporary Management of Patent Foramen Ovale," American Heart Association, Inc., Circulation, 2003, vol. 107, pp. 5-9.
Nat'l Aeronautics and Space Adminstration, "55-Nitinol- The Alloy with a Memory: Its Physical Metallurgy, Properties and Applications," NASA Report, pp. 24-25.
Ramanathan, G., et. al., "Experimental and Computational Methods for Shape Memory Alloys," 15th ASCE Engineering Mechanics Conference, Jun. 2-5, 2002.
Ruiz, et al., "The Puncture Technique: A New Method for Transcatheter Closure of Patent Foramen Ovale," Catheterization and Cardiovascular Interventions, 2001, vol. 53, pp. 369-372.
Shabalovskaya, S., "Surface Corrosion and Biocompatibility Aspects of Nitinol as and Implant Material," Bio-Medical Materials and Engineering, 2002, vol. 12, pp. 69-109.

SMST-2000, "Proceedings of the International Conference on Shape Memory and Superelastic Technologies," Apr. 30 to May 4, 2000, Asilomar Conference Center.
Stockel, "Nitinol Medical Devices and Implants," SMST-2000 Conference Proceedings, 2001, pp. 531-541.
Uchil, J., "Shape Memory Alloys—Characterization Techniques," Pramana—Journal of Physics, 2002 vol. 58 (5)(6), pp. 1131-1139.
Athanasion, T., "Coronary Artery Bypass with the Use of a Magnetic Distal Anastomotic Device: Surgical Technique and Preliminary Experience," The Heart Surgery Forum #2004-1024, 2004, 4 pgs.
Falk, V., "Facilitated Endoscopic Beating Heart Coronary Artery Bypass Grafting Using a Magentic Coupling Device," Journal of Thoracic and Cardiovascular Surgery, vol. 126,(5), pp. 1575-1579.
Filsoufi, F., et al., "Automated Distal Coronary Bypass with a Novel Magnetic Coupler (MVP system)," J. Thoracic and Cardiovascular Surgery, vol. 127(1), pp. 185-192.
Klima, U., "Magnetic Vascular Port Minimally Invasive Direct Coronary Artery Bypass Grafting," Circulation, 2004, II-55-II-60.
Stein, H., "Telemanipulator-gestützte Applikation eines magnetischen Gefäβ-Kopplers am schlagenden Herzen mit dem da Vinci™ -Surgical-System," Biomedizinische Technik, 2003, vol. 48(9), pp. 230-234.
Meditec, Ihre Datenbank für medizinisch-technisches Wissen, Fiz Technik.
Gruβwort zur gemeinsamen Jahrestagung der Öster-reichischen, Deutschen und Schweizerischen Gessellschaft für Biomedizinsche Technik, Sep. 24-27, 2003, St. Virgil/Salzburg.
Bachthaler, M. et al., "Corrosion of Tungsten Coils After Peripheral Vascular Embolization Theraphy: Influence on Outcome and Tungsten Load", Catherization and Cardiovascular Interventions, vol. 62, pp. 380-384, 2004.
Isotalo, T. et al., "Biocompatibility Testing of a New Bioabsorbable X-Ray Positive SR-PLA 96/4 Urethral Stent", The Journal of Urology, vol. 163, pp. 1764-1767, Nov. 1999.
Parviainen, M. et al., "A New Biodegradable Stent for the Pancreaticojejunal Anastomosis After Pancreatiocoduodenal Resection: In Vitro Examination and Pilot Experiences in Humans", Pancreas, vol. 21, No. 1, pp. 14-21, 2000.
Ruddy, A.C. et al., "Rheological, Mechanical and Thermal Behaviour of Radipaque Filled Polymers", Polymer Processing Research Centre, School of Chemical Engineering, Queen's University of Belfast , 5 pages.
Vaajanen, A. et al., "Expansion and Fixation Properties of a New Braided Biodegradable Urethral Stent: An Experimental Study in the Rabbit", The Journal of Urology, vol. 169, pp. 1771-1774, Mar. 2003.
International Search Report, International Application No. PCT/US03/35479, mailed Apr. 14, 2004 (2 pgs).
International Search Report, International Application No. PCT/US97/17927, mailed Feb. 10, 1998 (1 pg).
International Search Report, International Application No. PCT/US04/029978, mailed Jan. 26, 2005 (3 pgs).
International Search Report, International Application No. PCT/US04/026998, mailed Apr. 22, 2005 (5 pgs).
International Search Report, International Application No. PCT/US05/015382, mailed Oct. 6, 2005 (4 pgs).
International Search Report, International Application No. PCT/US2006/009978, mailed Jul. 13, 2006 (2 pgs).
International Search Report, International Application No. PCT/US03/39253, mailed Apr. 19, 2004 (4 pgs).
International Search Report, International Application No. PCT/US03/17715, mailed Mar. 24, 2004 (2 pgs).
International Search Report, International Application No. PCT/US97/14822, mailed Feb. 20, 1998 (2 pgs).
International Search Report, International Application No. PCT/US03/09051, mailed Sep. 29, 2003 (2 pgs).
International Search Report, International Application No. PCT/US03/01050, mailed Jul. 8, 2003 (1 pg).
International Search Report, International Application No. PCT/US02/40850 mailed Jun. 19, 2003 (4 pgs).
International Search Report, International Application No. PCT/US03/35998 mailed Jun. 16, 2004 (5 pgs).
International Search Report, International Application No. PCT/US03/32133, mailed Apr. 22, 2004 (1 pg).

International Search Report, International Application No. PCT/US03/34003 mailed Oct. 3, 2004 (4 pgs).

International Search Report, International Application No. PCT/US04/022643, mailed Mar. 31, 2005 (2 pgs).

International Search Report, International Application No. PCT/US05/006703, mailed Jul. 25, 2005 (3 pgs).

International Search Report, International Application No. PCT/US05/013705 mailed Aug. 4, 2005 (4 pgs).

International Search Report, International Application No. PCT/US06/009978, mailed Jul. 13, 2006 (2 pgs).

European Examination Report, European Application No. 03779297.5, mailed Mar. 15, 2007 (6 Pages).

European Examination Report, European Application No. 04781644.2, mailed Aug. 23, 2007 (3 Pages).

International Search Report for International Patent Application No. PCT/AU03/00759, filed Jun. 19, 2003.

International Search Report, International Application No. PCT/US03/35998 mailed Jun. 16, 2004 (5 pgs).

International Search Report, International Application No. PCT/US05/34276, mailed Oct. 9, 2007. (1 pg).

International Search Report, International Application No. PCT/US07/065546, mailed Oct. 29, 2007. (4 pages.).

International Search Report, International Application No. PCT/US2007/065526, mailed Aug. 8, 2007 (5 pgs).

International Search Report, International Application No. PCT/US2007/065541, mailed Aug. 7, 2007 (4 pgs).

* cited by examiner

EXPANDABLE SHEATH TUBING

CROSS-REFERENCE TO RELATED APPLICATION

This application claims priority to provisional application No. 60/421,436, filed Oct. 25, 2002, which is incorporated herein by reference.

BACKGROUND OF THE INVENTION

In many minimally invasive cardiac procedures, an introducer sheath may be placed in a vessel to gain access to a surgical site. Sheaths are used as conduits to pass surgical instruments or implantable devices through them. It is generally desirable to minimize the outer diameter of the sheath and maximize the inner diameter of the sheath. A small outer diameter is desired to minimally disrupt the circulatory pathway and is sometimes based on the anatomical size of the vessel it is designed to access. The inner diameter is designed as necessary for the surgical instrument or implant device to pass through it. An example of a catheter shown with a "daisy occluder" folded down for delivery within the catheter is shown in U.S. Pat. No. 5,741,297.]

SUMMARY OF THE INVENTION

A sheath can be formed in two or more layers with an inner layer made of a higher durometer (more rigid), less elastic material and an outer layer made of a lower durometer (softer), more elastic material. The inner layer can have one or a combination of the following: one or more longitudinal slits, overlapping circumferential portions, monolithic hinges, or other formations to allow for radial expansion. These formations can be present along a portion or the entire length of the sheath. Other materials can be added to the sheath, such as wires for strength, or the device can be made to have a minimal number of parts and portions.

The sheath can be an introducer sheath through which a guide wire and catheter are inserted, or the sheath can be a catheter or any other tubing inserted into a living body and through which other devices pass, such as stents, filters, occluders, or other devices. The sheath can be made by coextruding the layers, or with a dipping process.

In another embodiment, two materials can be used such that the materials alternate in a circumferential direction between more rigid, less elastic sections and softer, more elastic sections. In this case, the two materials can have the same wall thicknesses throughout the length of the sheath.

A radially expandable sheath allows a device to pass through a smaller diameter sheath than the device would otherwise be able, and thereby in a less invasive fashion. The sheath can be made smaller than the diameter of the device (at its maximum cross-section), so that the sheath expands slightly as the device passes through. With a brief radial expansion of the sheath, the trauma to the vessel through which it passes should be minimal. An expandable sheath can also be useful in retrieving a device from a body if the device, as folded for retrieval, has a larger diameter than it had when it was introduced into the body. Other features and advantages will become apparent from the drawings and detailed description.

DETAILED DESCRIPTION

In the embodiments of FIGS. 1-5, a relatively soft (lower durometer), more elastic outer material and a relatively rigid (higher durometer), less elastic inner material are coaxial, and preferably extruded, to form a tubular sheath that can expand radially, preferably for brief periods while a device is passed through, while not allowing significant longitudinal expansion. This capability allows a smaller diameter sheath to be used to deliver a device with a larger diameter, or allows a retrievable device to be withdrawn more easily if the device, in its retrieved state, has a larger diameter than in its delivered state, in each case while minimizing vessel occlusion. It is desirable for the vessel not to be enlarged, or if it does have to be enlarged, for it to happen for a minimal amount of time to allow the vessel to recover. The coextrusion of similar materials of differing durometer allows the inner layer and outer layer to bond thermally without significant delamination. Dissimilar materials could form a thermal bond or could be bonded through an intermediate layer. The more rigid material that makes up the inner layer can have one or more lengthwise slits filled in whole or in part with the softer material from the outer layer. The outer layer is entirely made of the softer material.

The layers should each be made of extrudable materials, such as polyether-block co-polyamide polymers, such as resins sold under the Pebax® name. Other combinations of materials for coextrusion can be used, such as a high density polyethylene for the rigid material, and a styrene-ethylene-butadiene block copolymer for the soft segment (such as C-Flex® or Kraton®). Other useful materials include silicone, polytetrafluoroethylene (PTFE), perfluoro (ethylene-propylene) copolymer (FEP), or urethane. It is generally desirable for the selected materials to melt together during the coextrusion process to prevent delamination. While many materials can be used, exemplary ranges for durometer on a Rockwell scale are 20-70 on the A scale for the outer material, and 60-80 on the D scale for the inner material. These ranges are only examples, and materials with other durometers could be used; for example, the material referred to as C-Flex is commercially offered in custom form with a durometer of 5-95 A.

Figure 1:
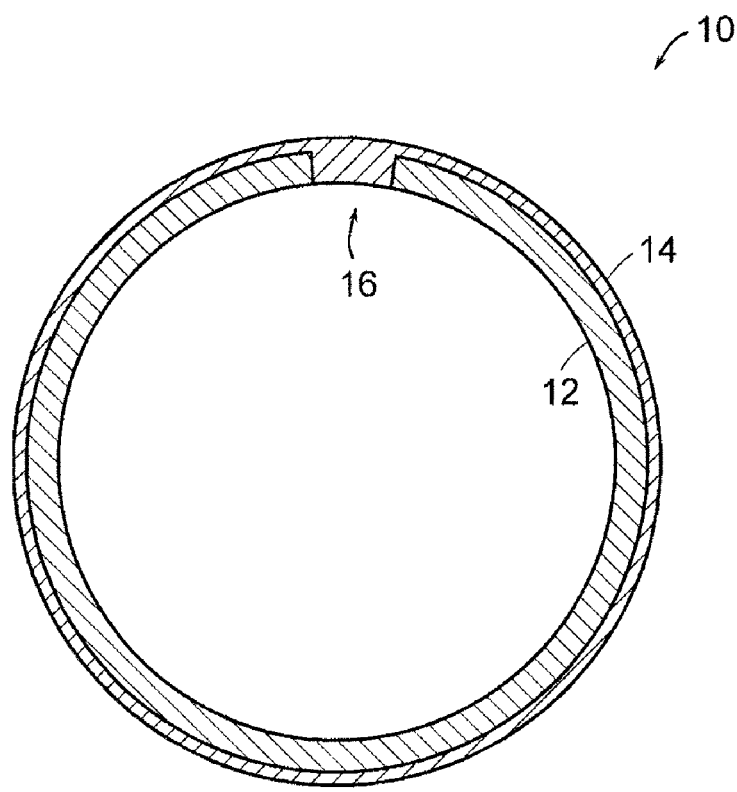
FIGS. 1-6 are cross-sectional views of a conduit according to various embodiments of the present invention.

Referring to FIG. 1, a sheath 10 has an inner layer 12 made of a relatively rigid material and an outer layer 14 made of a relatively soft material. Inner layer 12 has a longitudinal slit 16. During the coextrusion process, the softer material used to make outer layer 14 fills some or all of the gap created by slit 16. The slit provides some added flexibility for the inner layer. The device can be formed with one or more longitudinal slits that can extend for some or all of the length of the sheath.

In one embodiment, an inner layer is made of extruded Pebax 7233 with inner diameter 0.150" (3.8 mm) and outer diameter 0.166" (4.2 mm). The wall has a 0.023" (0.58 mm) wide lengthwise channel and it is overcoated with a softer extruded Pebax 2533 with outer diameter 0.174" (4.4 mm).

Figure 2:
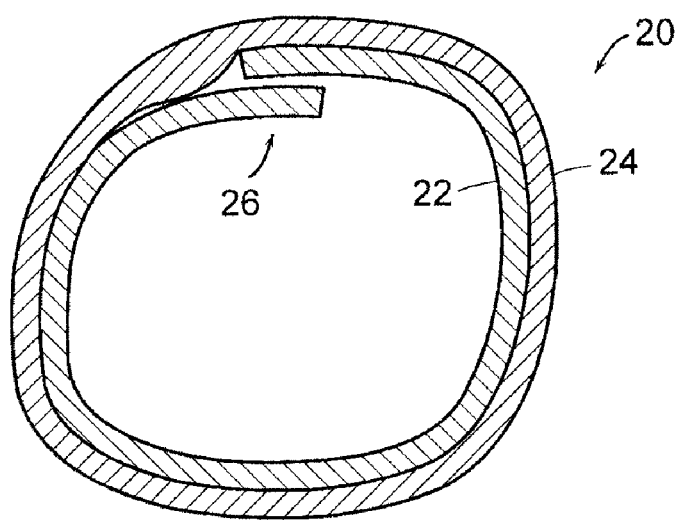

Referring to FIG. 2, a sheath 20 has an inner layer 22 and an outer layer 24. As with the sheath of FIG. 1 and the others described herein, the inner layer is made of a more rigid, higher durometer, less elastic material, while the outer layer is made of a softer, lower durometer, more elastic material. As shown here, inner layer 22 has an overlapping region 26 that provides some flexibility for inner layer 22 to expand. The softer outer layer 24 provides elasticity to allow some radial expansion. In other words, the inner layer is made of a less elastic material but has a formation to assist in its ability to expand radially, while the outer layer is made of a more elastic material.

Figure 3:
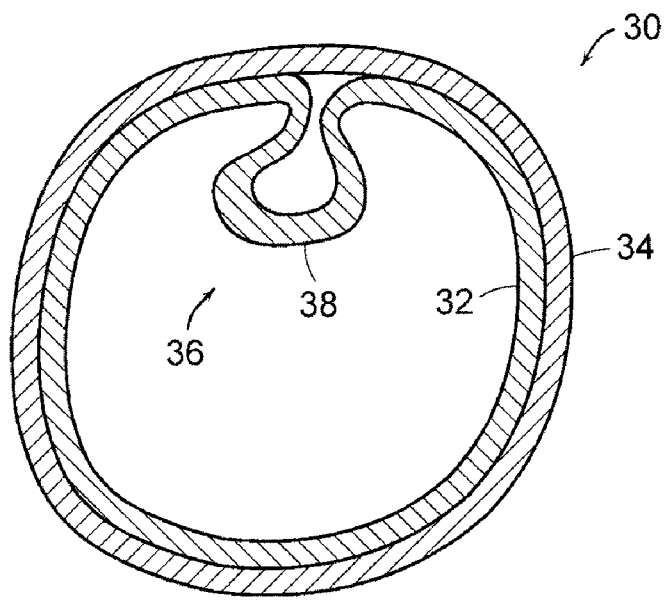

Referring to FIG. 3, sheath 30 has an inner layer 32, an outer layer 34, and a hinge 36. Hinge 36 is integral, and preferably monolithic, with respect to inner layer 32, and has symmetric curved portions that allow layer 32 to expand and allow hinge 36 to pivot about a pivot point 38 to expand the diameter.

Figure 4:
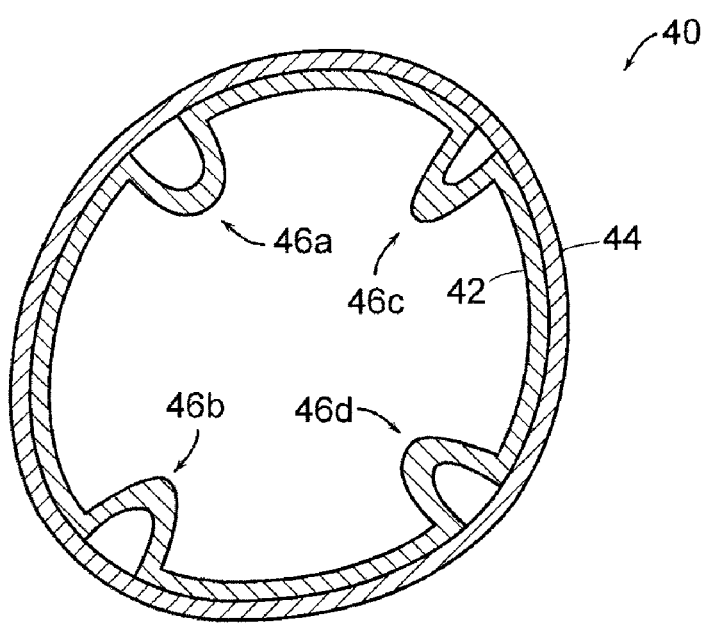

Referring to FIG. 4, a sheath 40 has an inner layer 42, an outer layer 44, and four integral, and preferably monolithic, hinges 46A-46D, each of which can allow inner layer 42 to expand radially. While four of these hinges are shown in FIG. 4, there could be two or more, and they could be evenly spaced about the circumference of inner layer 42 or spaced at irregular intervals as desired.

Figure 5:
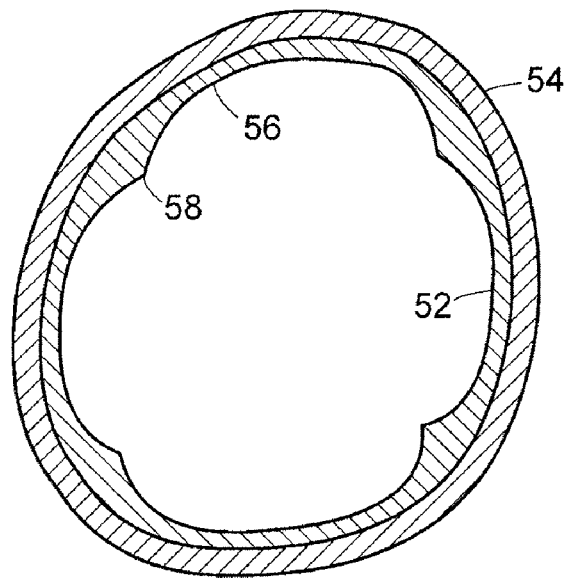

Referring to FIG. 5, an outer layer 54 surrounds an inner layer 52 which has reduced thickness portions 56 and greater thickness portions 58 spaced about the inner circumference of inner layer 52, thereby allowing layer 52 to expand. Four such greater thickness portions are shown, but there could be more or fewer.

In these embodiments described above, the inner layer typically has some geometric construction or formation, such as the use of a slit, overlapping portion, varying thickness, hinge, or other structure that gives the stiffer and less elastic inner layer more ability to expand radially than it otherwise would have. The outer layer is made of a softer and more elastic material, and therefore does not have as much need to have such geometric formations that assist in the expansion, although the outer layer could have some other formation and not necessarily be substantially just cylindrical as shown.

The sheaths described here are particularly useful for providing a conduit for other devices, such as stents, occluders, or guide wires, to be inserted into a human or non-human animal body. As is generally known, it is desirable for such a sheath to have as small a diameter as possible to minimize trauma to the vessel into which it is inserted. In the event some expansion to the vessel is required, it is desirable for it to be radial and short-term only to allow the vessel to recover its original shape.

Figure 7:
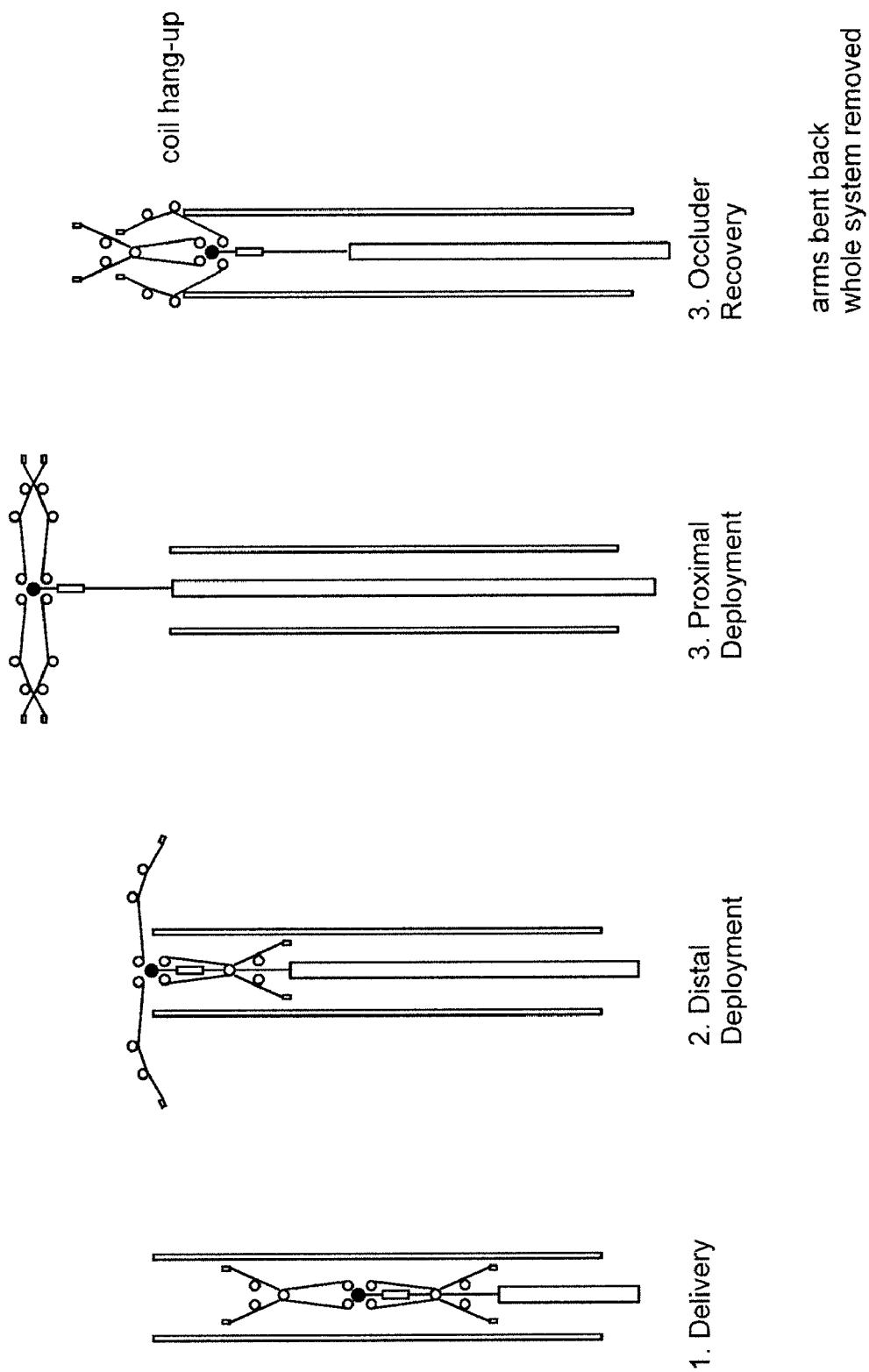
FIG. 7 has a series of partial cross-sectional, partial side views of a catheter with an occluder for delivery and for retrieval.

A sheath as described herein can be used with a device that is small enough to fit through the sheath without expanding the sheath, but which, if it is necessary to be retrieved, has a larger diameter (at least in some parts) on retrieval. Referring to FIG. 7, for example, a device, such as a patent foramen ovale (PFO) closure device or an occluder can have two connected hubs, each with radial spokes for supporting a fabric. This device has an appearance of two umbrellas, each concave and facing the other. For delivery, each of the "umbrellas" may be folded down separately within the catheter. These sides open up on distal and proximal deployment on opposite sides of a PFO or occlusion. If retrieved, the closure device may be folded in a configuration different from that in which it was delivered, e.g., such that the arms are bent back and the umbrellas overlap. Consequently, the cross-sectional diameter of the retrieved device passing through the conduit would be greater than the delivered device at some points. With the conduit of the present invention, the device could be delivered through the conduit without any expansion, but if retrieval is necessary during the procedure, the conduit can allow some temporary expansion for the device to pass through during retrieval. The conduit could also expand for both delivery and retrieval.

Many different diameters and thicknesses can be used to get the desired specifications for a particular application. Additional configurations of this embodiment may include longitudinal support structures such as wires that can be extruded as part of the inner and/or outer layers over all or part of the length of the layer. Wires can improve kink resistance while still enabling radial expansion of the tube.

A coating could be added to the inside and/or outside of the layers, such as a hydrophilic coating on the outer surface of the outer layer to assist with passage through the body if the outer layer is tacky. The lubricity provided by the coating can reduce the resistance to the device being pushed through the sheath.

While additional materials, such as longitudinal support wires, can be added, the sheath can be limited primarily to inner and outer layers, preferably coextruded, for use of fewer parts and steps and for ease of manufacture.

Figure 6:
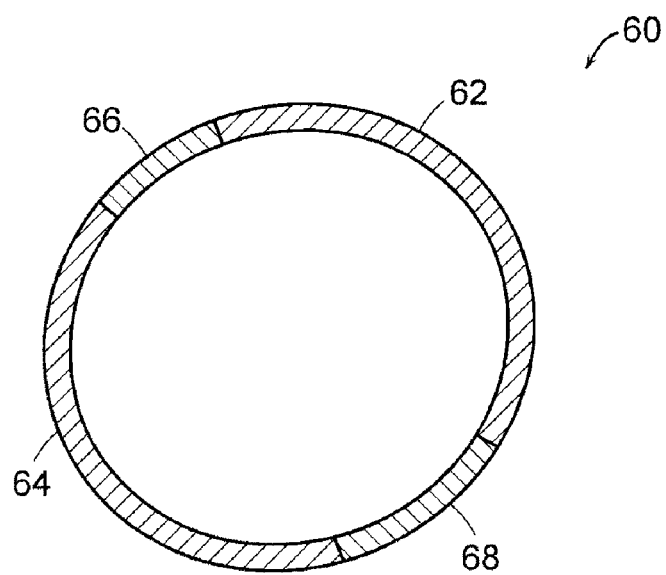

Another embodiment is shown in FIG. 6. As shown here, a sheath 60 has relatively rigid and less elastic sections 62 and 64, and relatively soft and more elastic sections 66 and 68, which essentially form stripes of soft material. In this case, the wall thickness can be substantially uniform, but with different materials in a circumferential direction. While two sectors each of rigid and soft are shown, more sectors could be provided, including one or more with still different durometer from the other two sectors. Like the embodiments of FIGS. 1-5, the conduit in this embodiment could temporarily expand as a device is passed through when delivered and/or retrieved.

The present invention thus includes designs for an expandable sheath, such as an introducer sheath or a catheter, that is inserted into a body, such as a human body; methods for making an expandable sheath, including coextrusion and dipping, to provide a sheath with radial flexibility; uses of such sheaths, such as for insertion into a body, such as a human body, to assist in delivering and/or retrieving a device, such as a stent, blood clot filter, or occluder, with at least a portion having a diameter greater than the inner diameter of the sheath when both are outside the body; and combinations of sheaths and devices as indicated above, including the combination of a sheath with a first inner diameter, and a device for passage through the sheath with at least a portion having a second diameter greater than the first diameter.

Accordingly, the present invention has been described with respect to exemplary embodiments of the present invention. It should be appreciated, though, that the present invention is defined by the following claims. Modifications or changes may be made to the exemplary embodiments of the present invention without departing from the inventive concepts contained herein or the scope of the claims.

What is claimed is:

1. A device comprising:
   a conduit for insertion into a living body, and through which another device passes, the conduit having inner and outer coaxial layers bonded together such that the outer layer surrounds the inner layer, wherein the durometer of the inner layer is greater than the durometer of the outer layer, the inner layer is discontinuous so as to form a longitudinal slit and is non-overlapping, and the outer layer is continuous, wherein a portion of the outer layer extends between the slit of the inner layer.

2. The device of claim 1, wherein the conduit is an introducer sheath.

3. The device of claim 1, wherein the conduit is a catheter.

4. The device of claim 1, wherein the slit of the inner layer allows the diameter of the inner layer to expand.

5. The device of claim 1, wherein the inner layer has a durometer in a range of 60-80 on the D scale.

6. The device of claim 5, wherein the outer layer has a durometer in a range of 20-70 on the A scale.

7. The device of claim 1, wherein the outer layer has a durometer in a range of 20-70 on the A scale.

8. The device of claim 1, further comprising a medical device for insertion through the conduit, the medical device having a portion with an outer diameter greater than the inner diameter of the inner layer, the conduit expanding temporarily and radially as the medical device is passed through.

9. The device of claim 8, wherein the medical device is selected from the group consisting of a stent, blood clot filter, or occluder.

10. The device of claim 1, further comprising a medical device for passing through the conduit,
the medical device being foldable in a first manner for delivery through the conduit and in a second manner different from the first manner for retrieval,
the cross-section of the device as folded in the second manner being greater than the cross-section of the device as folded in the first manner, the device as folded in the first manner having an outer diameter less than the inner diameter of the conduit, the device as folded in the second manner having an outer diameter greater than the inner diameter of the conduit, the conduit not expanding as the device is delivered and expanding temporarily and radially as the medical device is retrieved.

11. The device of claim 10, wherein the conduit is an introducer sheath.

12. The device of claim 10, wherein the conduit is a catheter.

13. A method comprising:
forming one of an introducer sheath or catheter through which a medical device is passed with inner and outer coaxial layers bonded together such that the outer layer surrounds the inner layer, wherein the elasticity of the outer layer is greater than the elasticity of the inner layer, the inner layer is discontinuous so as to form a longitudinal slit and is non-overlapping, and the outer layer is continuous; and
providing a portion of the outer layer to extend between the slit of the inner layer.

14. The method of claim 13, wherein the layers are bonded together through co-extrusion.

15. The method of claim 13, wherein the layers are bonded together through dipping.

16. The method of claim 13, wherein the slit of the inner layer allows the diameter of the inner layer to expand.

17. The method of claim 13, wherein the forming includes forming an introducer sheath.

18. The method of claim 13, wherein the forming includes forming a catheter.

19. A method comprising:
providing a medical device through a conduit in a living body, the conduit having inner and outer coaxial layers bonded together such that the outer layer surrounds the inner layer, the elasticity of the outer layer being greater than the elasticity of the inner layer, the inner layer being discontinuous so as to form a longitudinal slit and being non-overlapping, and the outer layer is continuous, a portion of the outer layer extending between the slit of the inner layer, and the conduit temporarily expanding in the radial direction as the device passes through.

20. The method of claim 19, wherein the medical device has an outer diameter greater than the inner diameter of the inner layer.

21. The method of claim 20, wherein the outer diameter of the device is greater when it is delivered.

22. The method of claim 20, wherein the outer diameter of the device is greater when it is retrieved, but not when it is delivered.

23. The device of claim 19, wherein the medical device is selected from the group consisting of a stent, blood clot filter, or occluder.

24. The method of claim 19, wherein the slit of the inner layer allows the inner layer to expand radially.

25. A device comprising:
a conduit for insertion into a living body, and through which another device passes, the conduit having at least one layer with first and second types of sections varying in a circumferential direction, the circumferential direction lying in a plane perpendicular to a longitudinal direction of the conduit, wherein the elasticity of one of the sections is greater than the elasticity of another one of the sections, the different elastic sections comprising resilient material and allowing the conduit to expand temporarily in the radial direction.

26. The device of claim 25, further comprising a medical device for insertion through the conduit, the medical device having a portion with an outer diameter greater than the inner diameter of the inner layer, the conduit expanding temporarily and radially as the medical device is passed through.

27. The device of claim 26, wherein the medical device is selected from the group consisting of a stent, blood clot filter, or occluder.

28. The device of claim 25, further comprising a medical device for passing through the conduit,
the medical device being foldable in a first manner for delivery through the conduit and in a second manner different from the first manner for retrieval,
the cross-section of the device as folded in the second manner being greater than the cross-section of the device as folded in the first manner, the device as folded in the first manner having an outer diameter less than the inner diameter of the conduit, the device as folded in the second manner having an outer diameter greater than the inner diameter of the conduit, the conduit not expanding as the device is delivered and expanding temporarily and radially as the medical device is retrieved.

29. The device of claim 25, wherein the conduit has a substantially uniform wall thickness.

30. The device of claim 25, wherein the at least one layer has third and fourth types of sections varying in a circumferential direction, wherein the elasticity of the third type of section is substantially equal to the elasticity of the first type of section and the elasticity of the fourth type of section is substantially equal to the elasticity of the second type of section.

31. The device of claim 30, wherein the second type of section is adjacent to both the first type of section and the third type of section.

32. A method comprising:
forming one of an introducer sheath or catheter through which a medical device is passed with at least one layer having first and second types of sections varying in a circumferential direction, the circumferential direction lying in a plane perpendicular to a longitudinal direction of the introducer sheath or catheter, wherein the elasticity of one of the sections is greater than the elasticity of another one of the sections, the different elastic sections comprising resilient material and allowing the conduit to expand temporarily in the radial direction.

33. The method of claim 32, wherein the at least one layer has third and fourth types of sections varying in a circumferential direction, wherein the elasticity of the third type of section is substantially equal to the elasticity of the first type of section and the elasticity of the fourth type of section is substantially equal to the elasticity of the second type of section.

34. The method of claim 33, wherein the second type of section is adjacent to both the first type of section and the third type of section.

35. The method of claim 32, wherein the forming includes forming an introducer sheath.

36. The method of claim 32, wherein the forming includes forming a catheter.

37. A method comprising:
providing a medical device through a conduit in a living body, the conduit having at least one layer with first and second types of sections in a circumferential direction, the circumferential direction lying in a plane perpendicular to a longitudinal direction of the conduit, wherein the elasticity of one of the sections is greater than the elasticity of another one of the sections, the different elastic sections comprising resilient material and allowing the conduit to expand temporarily in the radial direction.

38. The method of claim 37, wherein the at least one layer has third and fourth types of sections varying in a circumferential direction, wherein the elasticity of the third type of section is substantially equal to the elasticity of the first type of section and the elasticity of the fourth type of section is substantially equal to the elasticity of the second type of section.

39. The method of claim 37, wherein the second type of section is adjacent to both the first type of section and the third type of section.

40. The method of claim 37, wherein the medical device has an outer diameter greater than the inner diameter of the conduit.

41. The method of claim 40, wherein the outer diameter of the medical device is greater when it is delivered.

42. The method of claim 40, wherein the outer diameter of the medical device is greater when it is retrieved, but not when it is delivered.

43. The method of claim 37, wherein the medical device is selected from the group consisting of a stent, blood clot filter, or occluder.

* * * * *